(12) United States Patent
Boyd et al.

(10) Patent No.: US 7,309,698 B2
(45) Date of Patent: Dec. 18, 2007

(54) COMPOSITIONS FOR DELIVERING BISPHOSPHONATES

(75) Inventors: Maria Aurora P. Boyd, Garrison, NY (US); Steve Dinh, Briarcliff Manor, NY (US)

(73) Assignee: Emisphere Technologies, Inc., Tarrytown, NY (US)

( * ) Notice: Subject to any disclaimer, the term of this patent is extended or adjusted under 35 U.S.C. 154(b) by 124 days.

(21) Appl. No.: 10/468,622

(22) PCT Filed: Mar. 1, 2002

(86) PCT No.: PCT/US02/06295

§ 371 (c)(1),
(2), (4) Date: Aug. 19, 2003

(87) PCT Pub. No.: WO02/070438

PCT Pub. Date: Sep. 12, 2002

(65) Prior Publication Data

US 2004/0147484 A1   Jul. 29, 2004

Related U.S. Application Data

(60) Provisional application No. 60/272,676, filed on Mar. 1, 2001.

(51) Int. Cl.
*A61K 31/625* (2006.01)
*A61K 31/662* (2006.01)

(52) U.S. Cl. ............... 514/102; 514/104; 514/106; 514/108

(58) Field of Classification Search .......... 514/108, 514/102, 2; 562/444
See application file for complete search history.

(56) References Cited

U.S. PATENT DOCUMENTS

| | | | | |
|---|---|---|---|---|
| 4,814,326 A | * | 3/1989 | Rosini et al. | 514/108 |
| 5,616,571 A | * | 4/1997 | Daifotis et al. | 514/102 |
| 5,650,386 A | * | 7/1997 | Leone-Bay et al. | 514/2 |
| 5,773,647 A | * | 6/1998 | Leone-Bay et al. | 562/444 |
| 5,866,536 A | * | 2/1999 | Leone-Bay et al. | 514/2 |
| 6,693,208 B2 | * | 2/2004 | Gscheidner et al. | 554/1 |

FOREIGN PATENT DOCUMENTS

| | | | |
|---|---|---|---|
| WO | 97/36480 | | 10/1997 |
| WO | 00/06534 | | 2/2000 |
| WO | WO 00/06184 | * | 2/2000 |
| WO | 00/50386 | | 8/2000 |
| WO | 00/61111 | | 10/2000 |
| WO | 01/32596 | | 5/2001 |
| WO | 01/70219 | | 9/2001 |
| WO | 02/19969 | | 3/2002 |

OTHER PUBLICATIONS http://my.webmd.com/hw/osteoporosis/hw131588.asp.*
http://health.yahoo.com/ency/adam/000360/treatment.*
Saag et al., *New England Journal of Medicine* 339(5):292-299 (1998).
Partial European Search Report dated Feb. 12, 2007, issued for corresponding European Patent Application No. 02723294.

* cited by examiner

*Primary Examiner*—Raymond J. Henley, III
(74) *Attorney, Agent, or Firm*—Darby & Darby P.C.

(57) ABSTRACT

Compounds and compositions for the delivery of bisphosphonates are provided. Methods of preparation, administration and treatment are provided as well.

40 Claims, No Drawings

COMPOSITIONS FOR DELIVERING BISPHOSPHONATES

This application claims the benefit of U.S. Provisional Application No. 60/272,676, filed Mar. 1, 2001, which is hereby incorporated by reference.

FIELD OF THE INVENTION

The present invention relates to compounds and compositions for delivering bisphosphonates to a target. These compounds are well suited for forming non-covalent mixtures with bisphosphonates for oral administration to animals. Methods for preparation, administration and treatment are also disclosed.

BACKGROUND OF THE INVENTION

Conventional means for delivering active agents are often severely limited by biological, chemical, and physical barriers. Typically, these barriers are imposed by the environment through which delivery occurs, the environment of the target for delivery, and/or the target itself. Biologically and chemically active agents are particularly vulnerable to such barriers.

In the delivery to animals of biologically active and chemically active pharmacological and therapeutic agents, barriers are imposed by the body. Examples of physical barriers are the skin, lipid bi-layers and various organ membranes that are relatively impermeable to certain active agents but must be traversed before reaching a target, such as the circulatory system. Chemical barriers include, but are not limited to, pH variations in the gastrointestinal (GI) tract and degrading enzymes.

These barriers are of particular significance in the design of oral delivery systems. Oral delivery of many biologically or chemically active agents would be the route of choice for administration to animals if not for biological, chemical, and physical barriers that prevent, restrict or reduce the passage of active agents. Among the numerous agents in this category are bisphosphonates. Bisphosphonates are routinely prescribed for the treatment and/or prevention of osteoporosis. (See Drug Delivery Today, Yates, A. John and Rodan, Gideon "Alendronate and Osteoporosis" vol 3 No.; 2 pgs 69-78 February, 1998) Although some bisphosphonates are currently available in oral tablet dosage forms, the mean oral bioavailability relative to an intravenous (IV) reference dose is low; for example, alendronate has a reported mean bioavailability of 0.7% for doses ranging from 5 to 40 mg when administered after an overnight fast. Earlier methods for orally administering vulnerable pharmacological agents have relied on the co-administration of adjuvants (e.g., resorcinols and non-ionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. Liposomes have also been described as drug delivery systems for insulin and heparin. However, broad spectrum use of such drug delivery systems is precluded because: (1) the systems require toxic amounts of adjuvants or inhibitors; (2) suitable low molecular weight cargos, i.e. active agents, are not available; (3) the systems exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

Certain modified amino acids have been used to deliver pharmaceuticals. See, for example, U.S. Pat. Nos. 5,629,020; 5,643,957; 5,650,386; 5,766,633; 5,776,888; and 5,866,536; and PCT application WO00/06534.

There is a need for simple, inexpensive delivery systems which are easily prepared for the delivery of bisphosphonates.

SUMMARY OF THE INVENTION

The present invention provides compositions comprising at least one of the delivery agent compounds of the following formulas and at least one bisphosphonate. These compositions facilitate the delivery of the bisphosphonate to selected biological systems and increase or improve the bioavailability of bisphosphonate compared to administration without the delivery agent compound. Delivery agent compounds of the present invention include those having the following formulas or salts thereof:

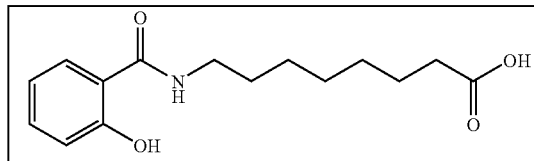

Compound 1

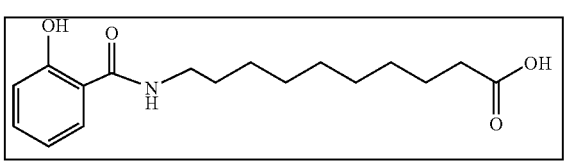

Compound 2

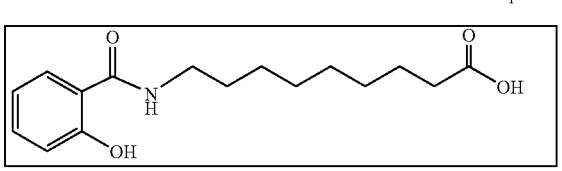

Compound 3

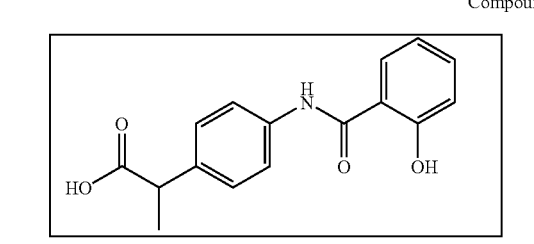

Compound 4

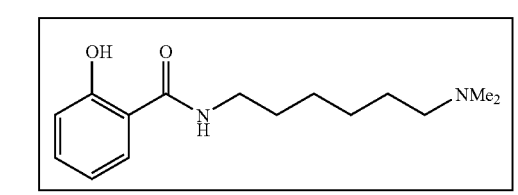

Compound 5

-continued

Compound 6

[Structure: 2-acetylphenyl ether with heptanoic acid chain]

Compound 7

[Structure: 2-hydroxyphenyl ether with hexanoic acid chain]

Compound 8

[Structure: 4-hydroxyphenyl ether with heptanoic acid chain]

Compound 9

[Structure: 5-chloro-2-hydroxybenzamide with hexanoic acid chain]

Compound 10

[Structure: 5-chloro-2-O⁻Na⁺ benzamide with heptanoic acid chain]

In another preferred embodiment, the composition comprises a bisphosphonate and a delivery agent of the following structure and salts thereof:

Compound A $$2\text{—HO—Ar—}\overset{O}{\overset{\|}{C}}\text{—NR}^8\text{—R}^7\text{—}\overset{O}{\overset{\|}{C}}\text{—OH}$$

wherein Ar is phenyl or naphthyl; optionally substituted with OH, halogen, $C_1$-$C_4$ alkyl, $C_1$-$C_4$ alkenyl, $C_1$-$C_4$ alkoxy or $C_1$-$C_4$ haloalkoxy;

$R^7$ is selected from the group consisting of $C_4$-$C_{20}$ alkyl, $C_4$-$C_{20}$ alkenyl, phenyl, naphthyl, ($C_1$-$C_{10}$ alkyl) phenyl, ($C_1$-$C_{10}$ alkenyl)phenyl, ($C_1$-$C_{10}$ alkyl) naphthyl, ($C_1$-$C_{10}$ alkenyl) naphthyl, phenyl ($C_1$-$C_{10}$ alkyl), phenyl ($C_1$-$C_{10}$ alkenyl), naphthyl ($C_1$-$C_{10}$ alkyl), or naphthyl ($C_1$-$C_{10}$ alkenyl);

$R^8$ is selected from the group consisting of hydrogen, $C_1$ to $C_4$ alkyl, $C_2$ to $C_4$ alkenyl, $C_1$ to $C_4$ alkoxy, $C_1$-$C_4$ and haloalkoxy;

$R^7$ is optionally substituted with $C_1$ to $C_4$ alkyl, $C_2$ to $C_4$ alkenyl, $C_1$ to $C_4$ alkoxy, $C_1$-$C_4$ haloalkoxy, —OH, —SH, and —$CO_2R^9$ or any combination thereof;

$R^9$ is hydrogen, $C_1$ to $C_4$ alkyl or $C_2$ to $C_4$ alkenyl.

$R^7$ is optionally interrupted by oxygen, nitrogen, sulfur or any combination thereof;

with the proviso that the compounds are not substituted with an amino group in the position alpha to the acid group or salts thereof.

According to one preferred embodiment, Ar is substituted with an OH. According another preferred embodiment, Ar is substituted with OH and halogen.

Preferably, $R^7$ is $C_4$-$C_{20}$ alkyl or phenyl ($C_1$-$C_{10}$ alkyl) More preferably $R^7$ is $C_5$-$C_{10}$ alkyl or phenyl ($C_2$ alkyl). Most preferably, $R^7$ is $C_7$-$C_9$ alkyl or phenyl($C_2$ alkyl).

Preferred carrier compounds are of the formulas of Compounds 1, 2, 3, 4 or salts thereof.

In another embodiment, the composition comprises a bisphosphonate and a delivery agent of the following structure and salts thereof:

Compound B $$2\text{—OH—Ar—}\overset{O}{\overset{\|}{C}}\text{—NH—R}^1\text{—R}^2$$

wherein

Ar is phenyl or naphthyl;

Ar is optionally substituted with $C_1$-$C_4$ alkyl, $C_1$-$C_4$ alkoxy, $C_2$-$C_4$ alkenyl, $C_2$-$C_4$ alkynyl, aryl, aryloxy, a heterocyclic ring, $C_5$-$C_7$ carbocyclic ring, halogen, —OH, —SH, $CO_2R^6$, —$NR^7R^8$, or —$N^+R^7R^8R^9Y^-$;

(a) $R^1$ is $C_1$-$C_{16}$ alkylene, $C_2$-$C_{16}$ alkenylene, $C_2$-$C_{16}$ alkynylene, $C_6$-$C_{16}$ arylene, ($C_1$-$C_{16}$ alkyl) arylene, or aryl ($C_1$-$C_{16}$ alkylene);

$R^2$ is —$NR^3R^4$ or —$N^+R^3R^4R^5Y^-$;

$R^3$ and $R^4$ are independently hydrogen; oxygen; hydroxy; substituted or unsubstituted $C_1$-$C_{16}$ alkyl; substituted or unsubstituted $C_2$-$C_{16}$ alkenyl; substituted or unsubstituted $C_2$-$C_{16}$ alkynyl; substituted or unsubstituted aryl; substituted or unsubstituted alkylcarbonyl; substituted or unsubstituted arylcarbonyl; substituted or unsubstituted alkanesulfinyl; substituted or unsubstituted arylsulfinyl; substituted or unsubstituted alkanesulfonyl; substituted or unsubstituted arylsulfonyl; substituted or unsubstituted alkoxycarbonyl; substituted or unsubstituted aryloxycarbonyl;

$R^5$ is independently hydrogen; substituted or unsubstituted $C_1$-$C_{16}$ alkyl; substituted or unsubstituted $C_2$-$C_{16}$ alkenyl; substituted or unsubstituted $C_2$-$C_{16}$ alkynyl; substituted or unsubstituted aryl; substituted or unsubstituted alkylcarbonyl; substituted or unsubstituted arylcarbonyl; substituted or unsubstituted alkanesulfinyl; substituted or unsubstituted arylsulfinyl; substituted or unsubstituted alkanesulfonyl; substituted or unsubstituted arylsulfonyl; substituted or unsubstituted alkoxycarbonyl; substituted or unsubstituted aryloxycarbonyl;

(b) $R^1$, $R^2$, and $R^5$ are as defined above; and $R^3$ and $R^4$ are combined to form a 5, 6 or 7-membered heterocyclic ring; or 5, 6 or 7-membered heterocyclic ring substituted with a $C_1$-$C_6$ alkyl, $C_1$-$C_6$ alkoxy, aryl, aryloxy, oxo group or carbocyclic ring; or (c) $R^2$ and $R^5$ are as defined above; and $R^1$ and $R^3$ are combined to form a 5, 6 or 7-membered heterocyclic ring; or 5, 6 or 7-membered heterocyclic ring substituted with a $C_1$-$C_6$ alkyl, alkoxy, aryl, aryloxy, or oxo group or carbocyclic ring;

$R^4$ is hydrogen; oxygen; hydroxy; substituted or unsubstituted $C_1$-$C_{16}$ alkyl; substituted or unsubstituted $C_2$-$C_{16}$ alkenyl; substituted or unsubstituted $C_2$-$C_{16}$ alkynyl; substituted or unsubstituted aryl; substituted or unsubstituted alkylcarbonyl; substituted or unsubstituted arylcarbonyl; substituted or unsubstituted alkanesulfinyl; substituted or unsubstituted arylsulfinyl; substituted or unsubstituted alkanesulfonyl; substituted or unsubstituted arylsulfonyl; substituted or unsubstituted alkoxycarbonyl; substituted or unsubstituted aryloxycarbonyl;

$R^6$ is hydrogen; $C_1$-$C_4$ alkyl; $C_1$-$C_4$ alkyl substituted halogen or —OH; $C_2$-$C_4$ alkenyl; or $C_2$-$C_4$ alkenyl substituted halogen or —OH;

$R^7$, $R^8$, and $R^9$ are independently hydrogen; oxygen; $C_1$-$C_4$ alkyl; $C_1$-$C_4$ alkyl substituted with halogen or —OH; $C_2$-$C_4$ alkenyl; or $C_2$-$C_4$ alkenyl substituted with halogen or —OH; and Y is halogen, hydroxide, sulfate, nitrate, phosphate, alkoxy, perchlorate, tetrafluoroborate, or caboxylate. A non-limiting example of a suitable carboxylate is acetate.

The term "substituted" as used herein with respect to compound B includes, but is not limited to, the following substituents: halogen and —OH.

In one preferred embodiment, Ar is unsubstituted phenyl or phenyl substituted with one or more of $C_1$-$C_4$ alkyl, $C_1$-$C_4$ alkoxy, or halogen; more preferably the phenyl is substituted with methoxy, Cl, F or Br.; more preferably the substitution is Cl.

In another preferred embodiment, $R^1$ is $C_1$-$C_{12}$ alkyl, more preferably $C_2$-$C_8$ alkyl, more preferably $C_2$-$C_6$ alkyl, and more preferably $C_6$ alkyl.

In another preferred embodiment, $R^3$ and $R^4$ are independently H or $C_1$-$C_2$ alkyl; more preferably $R^3$ and $R^4$ are not both H; more preferably $R^3$ and $R^4$ are independently methyl or ethyl; and more preferably $R^3$ and $R^4$ are both methyl.

In another preferred embodiment, the compound has the formula of Compound 5 or salts thereof.

Also provided are dosage unit forms comprising the compositions. The dosage unit may be in the form of a liquid or a solid, such as a tablet, capsule or particle, including a powder or sachet.

Another embodiment is a method for administering a bisphosphonate to an animal in need thereof, by administering a composition of the present invention to the animal. The preferred route of administration is oral.

Yet another embodiment is a method of treating and/or preventing bone-related disorders in an animal by administering the composition of the present invention to the animal. Typically, an effective amount of the composition is administered to treat and/or prevent the desired bone-related disorder.

Yet another embodiment is a method of preparing a composition of the present invention by mixing at least one delivery agent compound and at least one bisphosphonate.

DETAILED DESCRIPTION OF THE INVENTION

Delivery Agent Compounds

The terms "alkyl" and "alkenyl" as used herein include linear and branched alkyl and alkenyl substituents, respectively.

The delivery agent compounds depicted as carboxylic acids may be in the form of the carboxylic acid or salts thereof. Suitable salts include, but are not limited to, organic and inorganic salts, for example alkali-metal salts, such as sodium (e.g., monosodium and disodium salts, such as monosodium and disodium salts of compounds 1-4 and 7-9), potassium and lithium; alkaline-earth metal salts, such as magnesium, calcium or barium; ammonium salts; basic amino acids, such as lysine or arginine; and organic amines, such as dimethylamine or pyridine. Preferably, the salts are sodium salts. The salts may be mono- or multi-valent salts, such as monosodium salts and di-sodium salts. The salts may also be solvates, including ethanol solvates, and hydrates.

The delivery agent compounds depicted as amines may be in the form of the free amine or salts thereof. Suitable salts include, but are not limited to, organic and inorganic salts, for example hydrochloride salts, acetate or citrate.

Salts of the delivery agent compounds of the present invention may be prepared by methods known in the art. For example, sodium salts may be prepared by dissolving the delivery agent compound in ethanol and adding aqueous sodium hydroxide.

Where the delivery agent has an amine moiety and a carboxylic acid moiety, poly amino acids and peptides comprising one or more of these compounds may be used. An amino acid is any carboxylic acid having at least one free amine group and includes naturally occurring and synthetic amino acids. Poly amino acids are either peptides (which are two or more amino acids joined by a peptide bond) or are two or more amino acids linked by a bond formed by other groups which can be linked by, e.g., an ester or an anhydride linkage. Peptides can vary in length from dipeptides with two amino acids to polypeptides with several hundred amino acids.

One or more of the amino acids or peptide units may be acylated or sulfonated.

The compounds described herein may be derived from amino acids and can be readily prepared from amino acids by methods within the skill of those in the art, such as those described in WO96/30036, WO97/36480, WO00/06534, WO00/46812, WO00/50386, WO00/59863, WO 01/32596, WO 00/07979, U.S. Pat. No. 5,643,957, U.S. Pat. No. 5,650,386, and U.S. Pat. No. 5,866,536, all of which are incorporated by reference. For example, the compounds may be prepared by reacting the single amino acid with the appropriate acylating or amine-modifying agent, which reacts with a free amino moiety present in the amino acid to form amides. Protecting groups may be used to avoid unwanted side reactions as would be known to those skilled in the art. With regard to protecting groups, reference is made to T. W. Greene, *Protecting Groups in Organic Synthesis*, Wiley, N.Y. (1981), the disclosure of which is hereby incorporated herein by reference.

The delivery agent compound may be purified by recrystallization or by fractionation on one or more solid chromatographic supports, alone or linked in tandem. Suitable recrystallization solvent systems include, but are not limited to, acetonitrile, methanol, ethanol, ethyl acetate, heptane, water, tetrahydrofuran, and combinations thereof.

Fractionation may be performed on a suitable chromatographic support such as alumina, using methanol/n-propanol mixtures as the mobile phase; reverse phase chromatography using trifluoroacetic acid/acetonitrile mixtures as the mobile phase; and ion exchange chromatography using water or an appropriate buffer as the mobile phase. When anion exchange chromatography is performed, preferably a 0-500 mM sodium chloride gradient is employed.

Bisphosphonates

The term bisphosphonates refers to pyrophosphate analogs in which the central oxygen of the phosphorous-oxygen-phosphorous portion of the molecule, is replaced with a carbon to give a phosphorous-carbon-phosphorous moiety. Examples of bisphosphonates include but are not limited to alendronate, clodronate, etidronate, ibandronate, incadronate, minodronate, neridronate, olpadronate, pamidronate, risedronate, tiludronate, zoledronate, EB1053, YH529, and any analogs, mimetics, and polyethylene glycol-modified derivatives thereof.

Delivery Systems

The composition of the present invention comprises one or more delivery agent compounds and one or more bisphosphonate. In one embodiment, one or more of the delivery agent compounds is mixed with one or more bisphosphonates prior to administration to form an administration composition.

The administration compositions may be in the form of a liquid. The solution medium may be water. Dosing solutions may be prepared by mixing a solution of the delivery agent compound with a solution of the bisphosphonate, just prior to administration. Alternately, a solution of the delivery agent compound (or bisphosphonate) may be mixed with the solid form of the bisphosphonate (or delivery agent compound). The delivery agent compound and the bisphosphonate may also be mixed as dry powders. The delivery agent compound and the bisphosphonate can also be admixed during the manufacturing process.

The dosing solutions may optionally contain additives such as phosphate buffer salts, citric acid, glycols, or other dispersing agents. Stabilizing additives may be incorporated into the solution, preferably at a concentration ranging between about 0.1 and 20% (w/v)

The administration compositions may alternately be in the form of a solid, such as a tablet, capsule or particle, such as a powder or sachet. Solid dosage forms may be prepared by mixing the solid form of the compound with the solid form of the bisphosphonate. Alternately, a solid may be obtained from a solution of delivery agent compound and bisphosphonate by methods known in the art, such as freeze-drying (lyophilization), precipitation, crystallization and solid dispersion.

The administration compositions of the present invention may also include one or more enzyme inhibitors. Such enzyme inhibitors include, but are not limited to, compounds such as actinonin or epiactinonin and derivatives thereof. Other enzyme inhibitors include, but are not limited to, aprotinin (Trasylol) and Bowman-Birk inhibitor.

The amount of bisphosphonate used in an administration composition of the present invention is an amount effective to accomplish the purpose of the bisphosphonate for the target indication. The amount of bisphosphonate in the compositions typically is a pharmacologically, biologically, therapeutically, or chemically effective amount. However, the amount can be less than that amount when the composition is used in a dosage unit form because the dosage unit form may contain a plurality of delivery agent compound/bisphosphonate compositions or may contain a divided pharmacologically, biologically, therapeutically, or chemically effective amount.

The total effective amount can then be administered in cumulative units containing, in total, an effective amount of bisphosphonate.

The total amount of bisphosphonate to be used can be determined by methods known to those skilled in the art. However, because the compositions of the invention may deliver bisphosphonate more efficiently than compositions containing the bisphosphonate alone, lower amounts of bisphosphonate than those used in prior dosage unit forms or delivery systems can be administered to the subject, while still achieving the same blood levels and/or therapeutic effects.

The presently disclosed delivery agent compounds facilitate the delivery of bisphosphonate, particularly in oral form, but may also be useful in intranasal, sublingual, intraduodenal, subcutaneous, buccal, intracolonic, rectal, vaginal, mucosal, pulmonary, transdermal, intradermal, parenteral, intravenous, intramuscular and ocular systems.

Dosage unit forms can also include any one or combination of excipients, diluents, disintegrants, lubricants, plasticizers, colorants, flavorants, taste-masking agents, sugars, sweeteners, salts, and dosing vehicles, including, but not limited to, water, 1,2-propane diol, ethanol, olive oil, or any combination thereof.

The compounds and compositions of the subject invention are useful for administering bisphosphonates to any animals, including but not limited to birds such as chickens; and mammals, such as rodents, cows, pigs, dogs, cats, primates, and particularly humans.

The system is particularly advantageous for delivering bisphosphonates that would otherwise be destroyed or rendered less effective by conditions encountered before the bisphosphonate reaches its target zone (i.e. the area in which the bisphosphonate is to be released) and within the body of the animal to which they are administered. Particularly, the compounds and compositions of the present invention are useful in orally administering bisphosphonates, especially those that are not ordinarily orally deliverable, or those for which improved delivery is desired.

The compositions of the present invention have utility in the delivery of bisphosphonates to selected biological systems and in increasing and/or improving the bioavailability of bisphosphonates compared to administration of bisphosphonates alone. Delivery and/or bioavailability can be increased and/or improved by delivering more of the bisphosphonate over a period of time, or in delivering more bisphosphonate at a specific time, or in delivering bisphosphonate in a particular time period (such as to effect quicker or delayed delivery) or in delivering bisphosphonate over a period of time (such as sustained delivery).

The composition of the present invention can be administered to treat and/or prevent any disease for which bisphosphonates are known to be capable of treating and/or preventing. Typically, an effective amount of the composition is administered to treat and/or prevent the desired disease.

Another embodiment of the present invention is a method for the treatment and/or prevention of bone-related disorders in an animal by administering the composition of the present invention to the animal. Typically, an effective amount of the composition is administered to treat and/or prevent the desired bone-related disorder. Bone-related disorders include, but are not limited to, disorders of the bone and disease states, and include but are not limited to osteoporosis, bone degeneration, Paget's disease, and/or osteoclast function (for example, inhibiting osteoclasts).

Specific indications for bisphosphonate can be found in the Physicians' Desk Reference ($54^{th}$ Ed., 2000, Medical Economics Company, Inc., Montvale, N.J.), which is herein incorporated by reference.

The appropriate amount of the bisphosphonate and delivery agent can be determined by methods known in the art.

Following administration, the bisphosphonate is taken up into the circulation. The bioavailability of the bisphosphonates is calculated from its excretion in the urine or in its uptake in bone, according to methods used in the art.

DESCRIPTION OF THE PREFERRED EMBODIMENTS

The following examples illustrate the invention without limitation. All parts are given by weight unless otherwise indicated.

Proton nuclear magnetic resonance ($^1H$ NMR) analyses for the compounds listed below were conducted on a 300 MHz Bruker spectrometer using dimethyl sulfoxide (DMSO-$d_6$) as the solvent unless otherwise indicated.

EXAMPLE 1

Compound Preparation

Preparation of Compound 1

Sodium N-salicyloyl-8-aminocaprylate

The sodium salt of Compound 1 may be prepared according to the methods of U.S. Pat. No. 5,650,386, WO00/46182 or WO00/59863.

Preparation of Compound 2

10-(N-salicyloylamino)decanoic acid

Compound 2 may be prepared according to the methods of U.S. Pat. No. 5,866,536, WO00/46182 or WO00/59863.

Preparation of Compound 3

9-(salicyloylamino)nonanoic acid

Compound 3 may be prepared according to the methods of U.S. Pat. No. 5,866,536, WO00/46182 or WO00/59863 using the appropriate starting materials.

Preparation of Compound 4

Preparation of 2-(4-(N-salicyloyl)aminophenyl)propionic acid

Compound 4 may be made by the following method:

A slurry of 58.6 g (0.355 mol) of 2-(4-aminophenyl) propionic acid and 500 mL of methylene chloride was treated with 90.11 mL (77.13 g, 0.710 mol) of trimethylsilyl chloride and was heated to reflux for 120 min. The reaction mixture was cooled to 0° C. and treated with 184.44 mL (107.77 g, 1.065 mol) of triethylamine. After stirring for 5 minutes, this mixture was treated with a solution of 70.45 g (0.355 mol) of O-acetylsalicyloyl chloride and 150 mL of methylene chloride.

The reaction mixture was warmed to 25° C. and stirred for 64 hours. The volatiles were removed in vacuo. The residue was stirred in 2N aqueous sodium hydroxide for one hour and acidified with 2M aqueous sulfuric acid. The solid was recrystallized twice from ethanol/water to give a tan solid. Isolation by filtration afforded 53.05 g of (52% yield) of 2-(4-(N-salicyloyl) aminophenyl) propionic acid. Solubility: 200 mg/mL (200 mg+350 μl 2N NaOH+650 μl $H_2O$, pH=7.67). Anal. Calculated: C=67.36, H=5.3, N=4.91. Found: C=67.05, H=5.25, N=4.72.

Preparation of Compound 4 Sodium Salt

Preparation of Sodium 2-(4-(N-salicyloyl)aminophenyl)propionate

The sodium salt of compound 4 may be made by the following method:

A solution of 53.05 g (0.186 mol) of 2-(4-(N-salicyloyl) aminophenyl) propionic acid and 300 mL of ethanol was treated with 7.59 g (0.190 mol) of NaOH dissolved in 22 mL of water. The reaction mixture was stirred for 30 minutes at 25° C. and for 30 minutes at 0° C. The resulting pale yellow solid was isolated by filtration to give 52.61 g of sodium 2-(4-(N-salicyloyl) aminophenyl) propionate. Solubility: 200 mg/mL clear solution, pH=6.85. Anal. Calculated: C=60.45, H=5.45, N=3.92, Na=6.43. Found: C=60.84, H=5.87, N=3.85, Na=6.43. Melting point 236-238° C.

Preparation of Compound 5

N-(6-Dimethylaminohexyl)salicylamide

Compound 5 may be made by the following method:

A slurry of 18.02 g (110 mmol) of carsalam, 18.0 mL (15.84 g, 109 mmol) of 6-dimethylamino-1-hexanol, 29.12g (111 mmol) of triphenylphosphine,. and 150 mL of tetrahydrofuran was treated with a solution of 21.8 mL (22.39 g, 111 mmol) of diisopropyl azodicarboxylate and 40 mL of tetrahydrofuran, added dropwise over 20 minutes, causing the temperature of the slurry to rise to about 67° C. The reaction mixture was allowed to cool back to about 25° C. and stir for about 20 hours. The solution was treated with 150 mL (300 mmol) of aqueous 2N sodium hydroxide and warmed to about 60° C. for about 90 minutes. The reaction mixture was washed with ethyl acetate (2×60 mL). The aqueous phase was acidified with 4% aqueous hydrochloric acid to a pH slightly less than about 0 and washed with ethyl acetate (2×60 mL). The pH of the aqueous phase was raised to about 4.5 with 50% aqueous potassium carbonate and washed with ethyl acetate (2×60 mL). The aqueous phase was treated with solid sodium bicarbonate and extracted with ethyl acetate (14×60 mL). The combined 14 ethyl acetate extracts were dried over sodium sulfate and concentrated to a viscous liquid. The liquid was taken up into a minimum amount of ethyl acetate, diluted with 100 ml of hexanes and treated in an ice bath with 150 mL of hexanes, causing a white solid to develop. A total of 13.65 g of N-(6-dimethylaminohexyl)salicylamide was isolated by filtration.

Preparation of Compound 6

8-(2-Acetylphenoxy)octanoic acid

Compound 6 may be prepared by the following method.

Potassium hydroxide (10.72 g, 191.1 mmol) was ground in a mortar until powdered, then added to a 250 mL round bottom flask containing 80 mL of dimethyl sulfoxide. The resulting mixture was stirred for 5 minutes, after which time 6.47 g (47.5 mmol) of 2-hydroxyacetophenone was added, immediately followed by 24.04 g (95.7 mmol) of ethyl 8-bromooctanoate. The reaction was stirred at room temperature for one hour. The orange reaction mixture was poured into 200 mL of distilled water, then extracted five times with 300 mL (total) of methylene chloride. The organic layers were washed with two 50 mL portions of water, then concentrated to give a bright yellow liquid.

The liquid was dissolved in 25 mL of dioxane. Aqueous sodium hydroxide (1N, 20 mL) was added, and the resulting liquid was stirred and heated (65° C.) for two hours. The reaction mixture was cooled to 0° C., acidified to pH 1 with concentrated aqueous hydrochloric acid, then extracted with two 100 mL portions of ethyl acetate. The organic layer was concentrated to give a bright yellow oil. The oil was crystallized with methanol:water (1:1), then recrystallized once with methanol:water (1:1), and once with methylene chloride:hexanes (1:4), to give 5.70 g (43.1%) of a pale yellow to off white solid. Melting point: 71.5-73.5° C.

Combustion analysis: % C: 69.04 (calc'd), 68.77 (found); % H: 7.97 (calc'd), 8.04 (found). $^1$H NMR Analysis: (d$_6$-DMSO):δ 12.0, s, 1H; 7.57, dd, 1H; 7.52, dt, 1H; 7.15, d, 1H; 7.00, dt, 1H; 4.09, t, 2H; 2.52, s, 3H; 2.20, t, 2H; 1.78, p, 2H; 1.46, m, 4H; 1.32, m, 4H.

Preparation of Compound 7

8-(2-Hydroxyphenoxy)octanoic acid

Compound 7 may be prepared by the following method.

A 200 mL round bottom flask was charged with 22.9 g (3 equiv.) of freshly ground potassium hydroxide and 100 mL of dimethyl sulfoxide. This mixture was stirred at 25° C. for 5 minutes. Catechol (15 g, 1 equiv.) was added followed immediately by ethyl 8-bromooctanoate (34.2 g, 1 equiv). This dark brown solution was then stirred at 25° C. for 2 hours.

Distilled water (100 mL) was added and this solution was heated to 85° C. for 2 hours. The mixture was cooled, acidified to pH~2 with concentrated aqueous hydrochloric acid, and extracted with ethyl acetate (300 mL×2). The combined organics were dried over magnesium sulfate, filtered and the solvent evaporated. The crude material was purified by silica gel chromatography using 30-60% ethyl acetate/hexanes as eluent. The desired product was collected and dried to give 6.6 g (19%) of 8-(2-hydroxyphenoxy) octanoic acid as an off-white solid. Melting point: 60-64° C. Combustion analysis: % C: 66.65 (calc'd), 66.65 (found); % H: 7.99 (calc'd), 8.10 (found). $^1$H NMR Analysis: (d$_6$-DMSO): δ 12.0 s, 1H; 8.8, s, 1H; 6.90-6.86, m, 1H; 6.80-6.76, m, 3 H; 3.92, t, 2H; 2.21 t, 2H; 1.75-1.66, m, 2H; 1.56-1.29, m, 8H.

Alternate Preparation of Compound 7

A 500 mL Erlenmeyer flask was charged with 28 g (4 equiv.) of powdered potassium hydroxide and 400 mL of dimethyl sulfoxide. This mixture was stirred at room temperature for 5 minutes. 2-Benzyloxyphenol (25 g, 1 equiv.) was added and followed immediately by addition of ethyl 8-bromooctanoate (37.6 g, 1.2 equiv). The resulting solution was stirred at room temperature for 2 hours.

The reaction mixture was poured into 200 mL of distilled water and heated to 80° C. for 3 hours. This mixture was then acidified with concentrated aqueous hydrochloric acid to a pH of approximately 2. An off-white solid precipitated. This solid was isolated by vacuum filtration and allowed to dry overnight at room temperature in vacuo. The material was then esterified by reacting the crude acid with 1L of methanol and 5 mL of sulfuric acid and subsequent heating to 80° C. overnight.

The mixture was cooled and extracted with ethyl acetate 3×400 mL, dried over magnesium sulfate, filtered and evaporated to give the methyl ester in quantitative yield.

The crude ester was then dissolved in 150 mL of ethanol and mixed with 1 g of 10% palladium on activated carbon. This mixture was placed in the Parr autoclave. The reaction vessel was then pressurized to 200 psi with hydrogen. The heterogeneous mixture was stirred at 50° C. for 18 hours. The palladium was filtered off and the filtrate concentrated to give the debenzylated product.

The methyl ester was saponified using 10 g of sodium hydroxide, 400 mL of methanol, and 50 mL of water. The solution was heated to 80° C. for one hour, and then allowed to stir at ambient temperature overnight. The methanol was evaporated. An additional 100 mL of water was added and the aqueous layer acidified with concentrated aqueous hydrochloric acid to a pH of 2. The aqueous phase was then extracted with ethyl acetate, 3×300 mL, dried and evaporated to give the target material. The crude material was then purified by silica gel chromatography using 30-60% ethyl acetate/hexanes, as eluent, to give 22.24 g (71%) of 8-(2-hydroxyphenoxy)octanoic acid as an off-white solid. Melting point: 65-68° C. Combustion analysis: % C: 66.65 (calc'd), 66.98 (found); % H: 7.99 (calc'd) 8.22 (found). $^1$H NMR Analysis: (d$_6$-DMSO): δ 12.0, s, 1H; 8.8, s, 1H; 6.90-6.87, m, 1H; 6.80-6.67, m, 3H; 3.94, t, 2H; 2.23, t, 2H; 1.73, p, 2H; 1.53-1.29, m, 8H.

Preparation of Compound 8

4-Hydroxyphenyl-8-oxyoctanoic acid

Compound 8 may be made by the following method:

Potassium hydroxide (11.20 g, 200.0 mmol) was ground in a mortar until powdered, then added to a 0.5 L round bottom flask containing 90 mL of DMSO. The resulting mixture was stirred for 5 minutes, after which time 10.00 g (50.0 mmol) of 4-benzyloxyphenol were added, immediately followed by 12.55 g (50.0 mmol) of ethyl 8-bromooctanoate. The reaction was stirred at room temperature for two and one half hours. The reaction mixture was poured into 200 mL of distilled water, and heating to reflux was initiated. This was allowed to continue heating for three and one half hours. Heating of the reaction mixture was then discontinued and the reaction mixture was allowed to come to room temperature overnight. Heating was restarted the following day when it was determined that the hydrolysis was incomplete. After an additional three-hour period of heating, it was determined that the reaction was completed and heating was discontinued. When the reaction mixture had cooled to room temperature, it was acidified with 2N, HCl solution and the resulting solid was isolated by filtration. The solid was allowed to dry under vacuum overnight. 17.96 g of the 4-benzyloxyphenyl-8-oxyoctanoic acid was isolated.

This material was used as is for the next step. The 4-benzyloxyphenyl-8-oxyoctanoic acid was placed into a 0.5 L round bottomed flask with 120 mL of ethyl alcohol. The mixture was sparged for 15 minutes with nitrogen before 10% palladium on activated carbon was added to the reaction mixture. The flask was then evacuated and a balloon containing hydrogen was placed atop the flask in a way that the contents of the flask were kept under a hydrogen atmosphere. This mixture was allowed to stir overnight at room temperature, and was then filtered through celite. Ethyl alcohol was removed in vacuo, yielding a white solid which was first recrystallized from 90:10 ethyl alcohol: water and then was dissolved in 2N NaOH. This mixture was filtered and acidified with 2N HCl. The resulting white solid was isolated by filtration and allowed to dry under vacuum. 2.12 g of the 4-hydroxyphenyl-8-oxyoctanoic acid was isolated. Melting point: 97-100° C. Combustion analysis: % C: 66.67 (calc.), 66.43 (found); % H: 7.94 (calc.), 7.80 (found). $^1$H NMR Analysis: (d$_6$-DMSO): δ 12.0, s, 1H; 9.00, s, 1H; 6.63, m, 4H; 3.75, t, 2H; 2.15, t, 2H; 1.60, p, 2H; 1.45, p, 2H; 1.20, m, 6H.

Preparation of Compound 10

N-(5-chlorosalicyloyl)-8-aminocaprylate

The disodium salt of Compound 10 may be prepared according to the methods of WO00/59863.

Example 2

Bisphosphonate Oral Delivery

Oral dosing (PO) compositions of delivery agent compound and alendronate (anhydrous, monosodium salt) in water were prepared. Typically 400 mg of delivery agent compound was added to 2.0 mL of water. When the delivery agent compound had a carboxylic acid terminal, either the sodium salt of the compound was used or the free acid was converted to the sodium salt by stirring the resultant solution and adding one equivalent of sodium hydroxide (10.0 N) and diluting with water. The solution was vortexed, then heated (about 37° C.) and sonicated. The pH was adjusted to about 7 (7.0 to 8.5) with NaOH or HCl. Additional NaOH (for carboxylic acid terminated delivery agents) or HCl (for amine terminated compounds) was added as necessary to achieve uniform solubility, and the pH readjusted. Water was then added to bring the total volume to about 2.5 mL (varies depending on solubility of the delivery agent compound). Alendronate (25 µl) from a stock solution (made from 2.0 g sodium alendronate in 10 ml deionized water, pH adjusted to about 7.5 with 10N NaOH, vortexed and sonicated at 37° C. to obtain a clear solution, frozen and defrosted before use) was added to the solution. The final doses were 200 mg/kg delivery agent compound (i.e. 200 mg delivery agent compound per kg of body weight) and 2.5 mg/kg alendronate, and the volume dose was 1.0 mL/kg.

The typical dosing and sampling protocols were as follows. Male Sprague-Dawley rats weighing between 200-250 g were fasted for 24 hours prior to dosing. For those experiments where the dosing was to non-fasted rats the animals had access to food and water ad libitum. A dosing group of five animals was administered one of the dosing solutions. For oral dosing, an 11 cm Rusch 8 French catheter was adapted to a 1 mL syringe with a pipette tip. The syringe was filled with dosing solution by drawing the solution through the catheter, which was then wiped dry. The catheter was placed down the esophagus leaving 1 cm of tubing past the incisors. Solution was administered by pressing the syringe plunger.

After dosing, the animals were housed singly in metabolism cages. Food was administered 45 minutes post-dosing. Water was available ad libitum. Urine collection commenced as soon as the animals were placed in their cages. Urine samples were taken at 14 hours post dose. The samples were stored on dry ice until sampled. Quantitation was by HPLC method for alendronate.

As a control, 0.1 mg/kg alendronate (from a 2 mL sterile water solution made from 120 µl of a solution made from the following: 3.33 mg sodium alendronate, 4.91 mg sodium chloride USP reagent crystals; 10.3 mg sodium citrate USP, 2.88 mg citric acid USP, in 10 mL deionized water, pH about 5.0.) was injected intravenously through the tail vein without anesthesia. Urine samples were collected as above. The results are illustrated in Table 1. ALN=alendronate.

TABLE 2

Oral Dose-Response: Alendronate and Compound 1

| Delivery Agent | Alendronate dose/Delivery Agent dose (mg/mg) per kg body weight | Average ALN in Urine[+] (ng) | Std. Dev. | n* | Range (ng) |
|---|---|---|---|---|---|
| (none) | 2.5 | 325.93 | 74.20 | 5 | 253.44-434.12 |
| 1 | 2.5/200 | 6093.18 | 4561.10 | 4 | 1097.56-11890.55 |
| 1 | 1.0/200 | 1584.53 | 1030.16 | 5 | 408.64-3227.36 |
| 1 | 0.50/200 | 1716.17 | 851.79 | 4 | 788.20-2746.00 |
| 1 | 0.25/200 | 806.44 | 541.43 | 3 | 349.96-1404.64 |
| 1 | 0.10/200 | 538.65 | 237.93 | 4 | 307.16-843.08 |

*n = number of samples that had reportable values of [ALN] out of 5
[+][ALN] in ng/mL times total amount of urine excreted 14 hours post dose
All animals were fasted for 24 hours.

TABLE 3

Oral Dose Response: Alendronate and Compound 10

| Delivery Agent | Alendronate dose/Delivery Agent dose (mg/mg) per kg body weight | Average ALN in Urine[+] (ng) | Std. Dev. | n* | Range (ng) |
|---|---|---|---|---|---|
| (none) | 5 | 188.42 | 68.9 | 5 | 105-253 |
| 9 | 5/200 | 1712.2 | 343.9 | 4 | 1354-2607 |
| 9 | 2.5/200 | 1017.67 | 176.73 | 5 | 490-1474 |
| 9 | 1.25/200 | 659.67 | 123.56 | 5 | 374-1103 |
| 9 | 0.62/200 | 343-83 | 102.81 | 5 | 86-812 |

[+][ALN] in ng/mL times total amount of urine excreted 14 hours post dose
All animals were fasted for 24 hours

TABLE 1

Efficacy of the Oral Delivery of Alendronate

| Delivery Agent Compound # | Route of administration | Average Amt. Of ALN Excreted* (ng) | Std. Dev. | n | Mean F[+] | Range (ng) |
|---|---|---|---|---|---|---|
| (none) | IV | 928.62 | 374.67 | 5 | 100.0 ± 1.61 | 392.28-1345.08 |
| (none) | PO | 110.96 | 35.44 | 10 | 0.48 ± 0.15 | 62.32-169.32 |
| 1 | PO | 6366.27 | 3269.43 | 5 | 27.42 ± 14.10 | 2632.77-10057.85 |
| 4 | PO | 5496.56 | 2401.44 | 5 | 23.68 ± 10.34 | 2376.68-8856.76 |
| 5 | PO | 2559.11 | 1616.03 | 5 | 11.02 ± 6.96 | 786.99-4544.08 |
| 6 | PO | 3180.87 | 1857.81 | 5 | 13.70 ± 8.00 | 889.44-5367.03 |
| 7 | PO | 2748.21 | 1474.64 | 5 | 11.84 ± 6.35 | 850.64-4300.44 |
| 8 | PO | 1448.01 | 892.86 | 5 | 6.23 ± 3.84 | 340.70-2578.03 |

[+]Mean Bioavailability relative to IV Reference Dose
*[ALN] times total amount of urine excreted 14 hours post-dose
Note:
Delivery Agent dose is 200 mg/kg
All animals were fasted for 24 hours.

TABLE 4

Oral Administration of Alendronate: Effects of Fasting

| Delivery Agent | Alendronate dose/Delivery Agent dose (mg/mg) per kg body weight | Average ALN in Urine[+] (ng) | Std. Dev. | n* | Fasted or non-Fasted |
|---|---|---|---|---|---|
| 1 | 2.5 | 50.88 | 14.18 | 5 | Fasted |
| 1 | 2.5 | 12.32 | 5.8 | 5 | non-Fasted |
| 1 | 2.5/200 | 609 | 192.1 | 5 | Fasted |
| 1 | 2.5/200 | 20.3 | 69.18 | 5 | non-Fasted |
| 9 | 2.5 | 47.88 | 14.56 | 5 | Fasted |
| 9 | 2.5 | 10.55 | 5.74 | 5 | non-Fasted |
| 9 | 2.5/200 | 1509 | 195.90 | 5 | Fasted |
| 9 | 2.5/200 | 210.13 | 150.44 | 5 | non-Fasted |

[+][ALN] in ng/mL times total amount of urine excreted 14 hours post dose

TABLE 5

Delivery Agent Dose Response: Alendronate and Compound 10

| Delivery Agent | Alendronate dose/Delivery Agent dose (mg/mg) per kg body weight | ALN Average in Urine[+] (ng) | Std. Dev. | n* |
|---|---|---|---|---|
| 9 | 2.5/0 | 147 | 98.3 | 5 |
| 9 | 2.5/200 | 1140.67 | 191.98 | 5 |
| 9 | 2.5/100 | 473.33 | 320.81 | 5 |
| 9 | 2.5/50 | 418.33 | 221.55 | 5 |
| 9 | 2.5/50 | 97 | 324.39 | 5 |

[+][ALN] in ng/mL times total amount of urine excreted 14 hours post dose
All animals were fasted for 24 hours The above mentioned patents, applications, test methods, and publications are hereby incorporated by reference in their entirety.

Many variations of the present invention will suggest themselves to those skilled in the art in light of the above detailed description. All such obvious variations are within the fully intended scope of the appended claims.

What is claimed is:
1. A composition comprising:
   (A) alendronate; and
   (B) at least one compound selected from

Compound 1

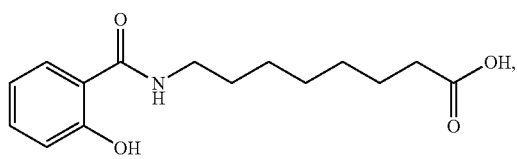

Compound 2

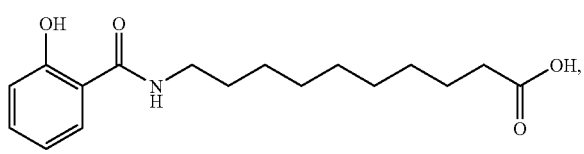

Compound 3

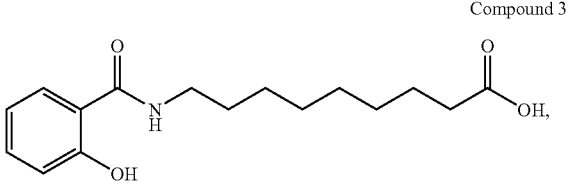

Compound 4

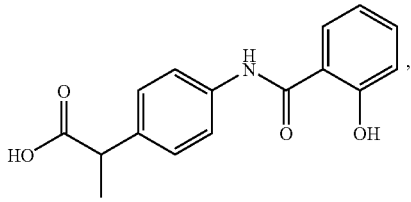

Compound 5

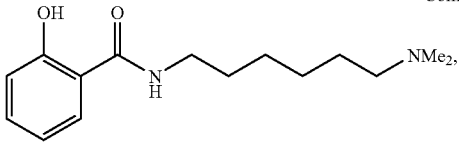

Compound 6

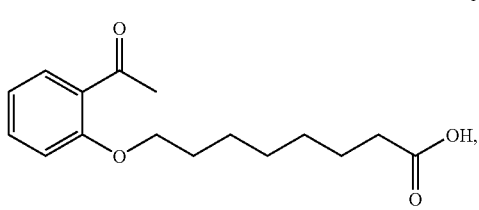

Compound 7

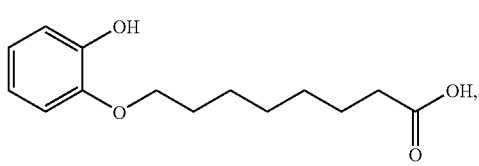

Compound 8

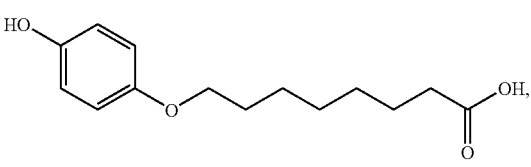

and salts thereof.

2. The composition of claim 1 wherein (B) is

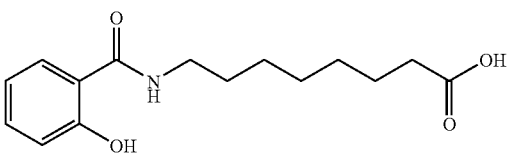

Compound 1 or a salt thereof.

3. The composition of claim 2 wherein (B) is the sodium salt of compound 1.

4. The composition of claim 1 wherein (B) is

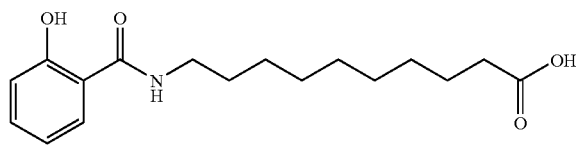

Compound 2 or a salt thereof.

5. The composition of claim 1 wherein (B) is

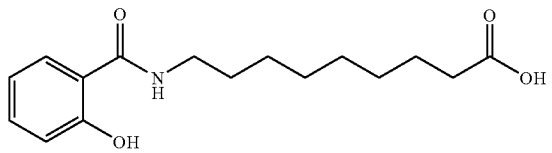

Compound 3 or a salt thereof.

6. The composition of claim 1 wherein (B) is

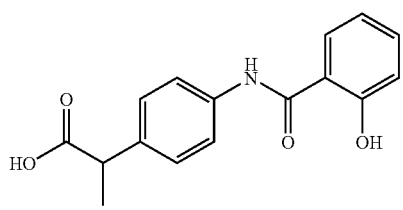

Compound 4 or a salt thereof.

7. The composition of claim 1 wherein (B) is

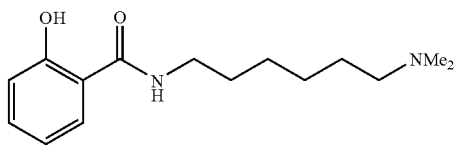

Compound 5 or a salt thereof.

8. The composition of claim 1 wherein (B) is

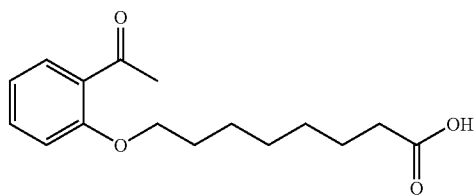

Compound 6 or a salt thereof.

9. The composition of claim 1 wherein (B) is

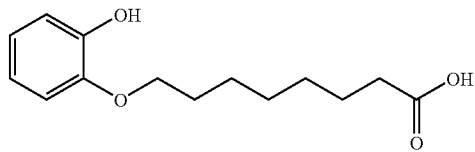

Compound 7 or a salt thereof.

10. The composition of claim 1 wherein (B) is

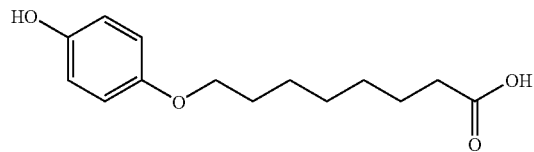

Compound 8 or a salt thereof.

11. A composition comprising:
(A) ibandronate; and
(B) at least one compound selected from

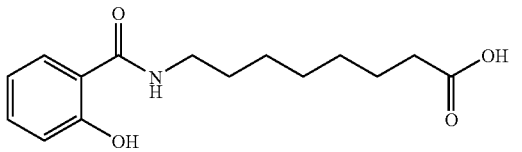

Compound 1,

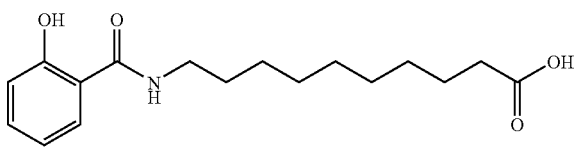

Compound 2,

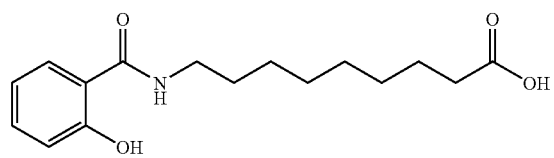

Compound 3,

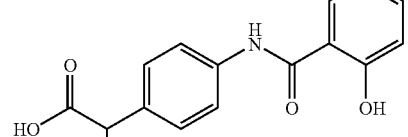

Compound 4,

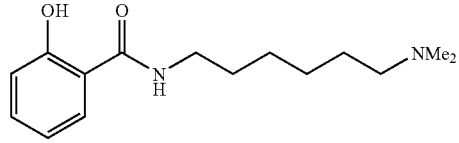

Compound 5,

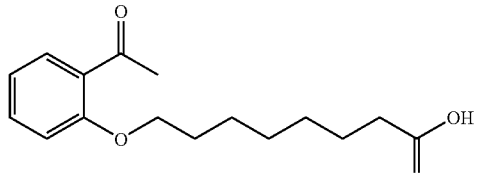

Compound 6,

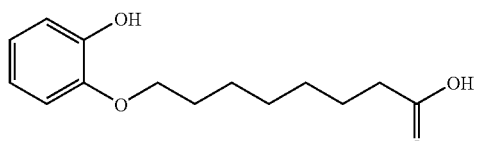

Compound 7,

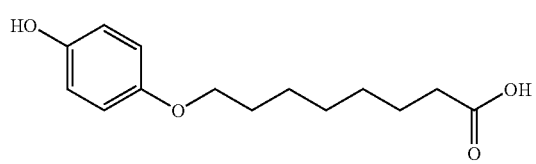

Compound 8, and salts thereof.

12. The composition of claim 11 wherein (B) is

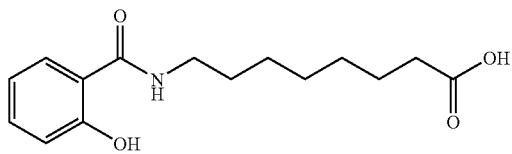

Compound 1 or a salt thereof.

13. The composition of claim 12 wherein (B) is the sodium salt of compound 1.

14. The composition of claim 11 wherein (B) is

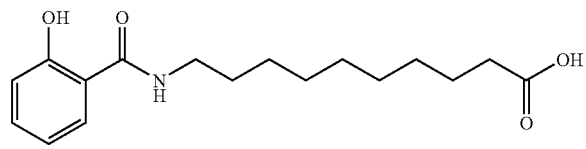

Compound 2 or a salt thereof.

15. The composition of claim 11 wherein (B) is

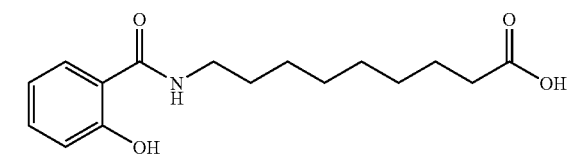

Compound 3 or a salt thereof.

16. The composition of claim 11 wherein (B) is

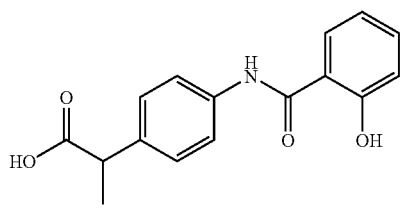

Compound 4 or a salt thereof.

17. The composition of claim 11 wherein (B) is

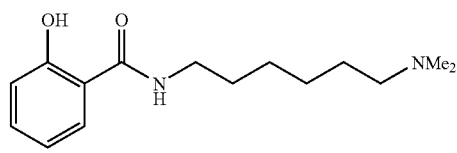

Compound 5 or a salt thereof.

18. The composition of claim 11 wherein (B) is

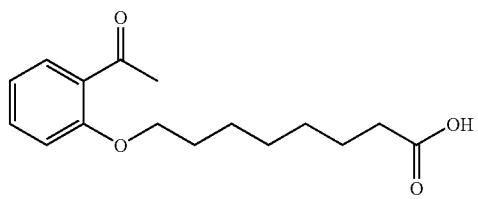

Compound 6 or a salt thereof.

19. The composition of claim 11 wherein (B) is

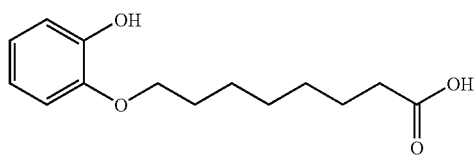

Compound 7 or a salt thereof.

20. The composition of claim 11 wherein (B) is

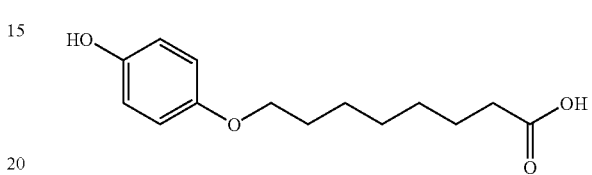

Compound 8 or a salt thereof.

21. A composition comprising:
(A) risedronate; and
(B) at least one compound selected from Compound 1,

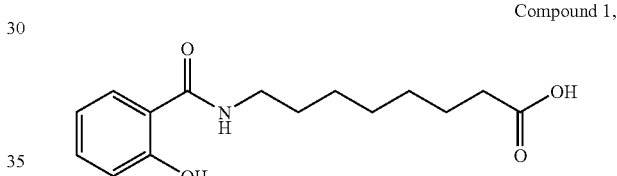

Compound 2,

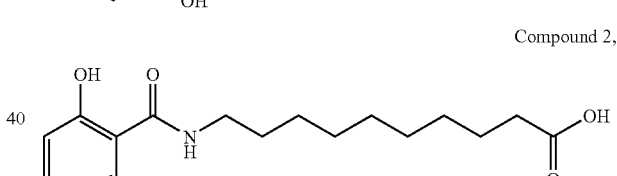

Compound 3,

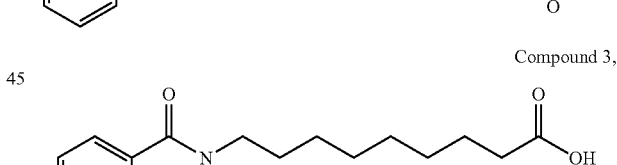

Compound 4,

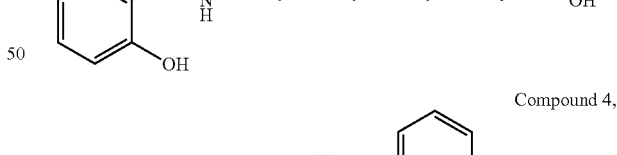

Compound 5,

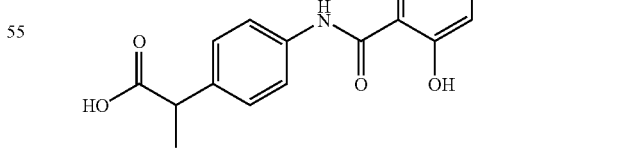

-continued

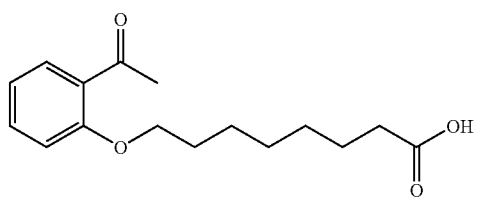

Compound 6,

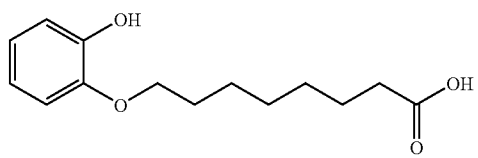

Compound 7,

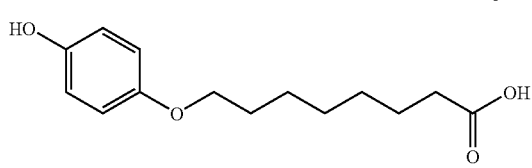

Compound 8, and salts thereof.

22. The composition of claim 21 wherein (B) is

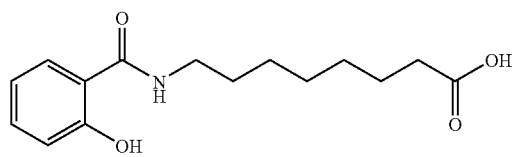

Compound 1 or a salt thereof.

23. The composition of claim 22 wherein (B) is the sodium salt of compound 1.

24. The composition of claim 21 wherein (B) is

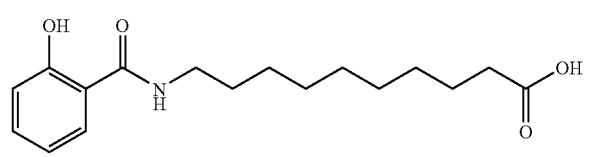

Compound 2 or a salt thereof.

25. The composition of claim 21 wherein (B) is

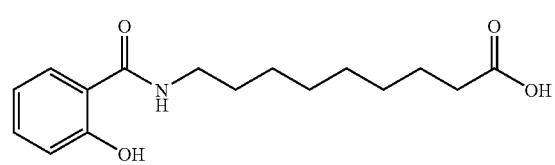

Compound 3 or a salt thereof.

26. The composition of claim 21 wherein (B) is

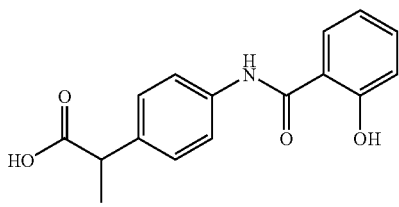

Compound 4 or a salt thereof.

27. The composition of claim 21 wherein (B) is

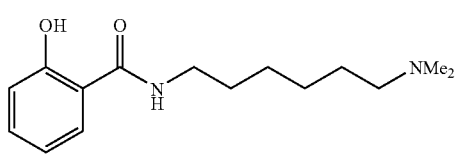

Compound 5 or a salt thereof.

28. The composition of claim 21 wherein (B) is

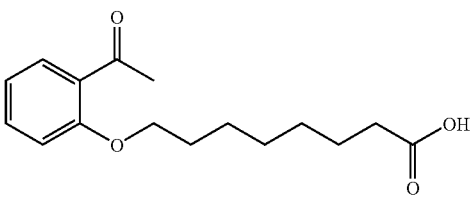

Compound 6 or a salt thereof.

29. The composition of claim 21 wherein (B) is

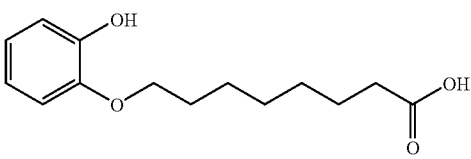

Compound 7 or a salt thereof.

30. The composition of claim 21 wherein (B) is

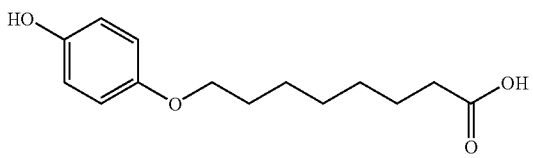

Compound 8 or a salt thereof.

31. A composition comprising:
(A) zoledronate; and
(B) at least one compound selected from Compound 1,

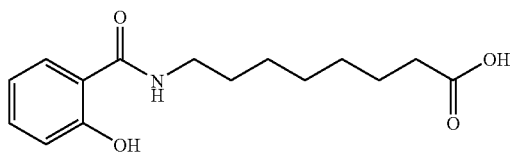

Compound 2,

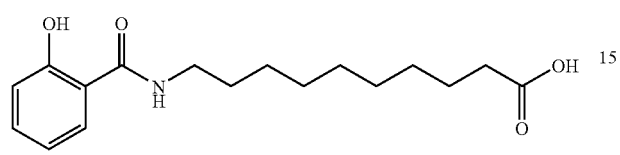

Compound 3,

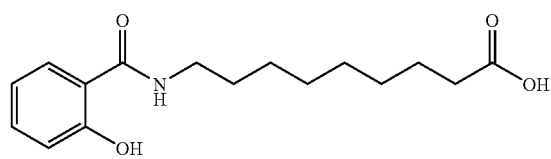

Compound 4,

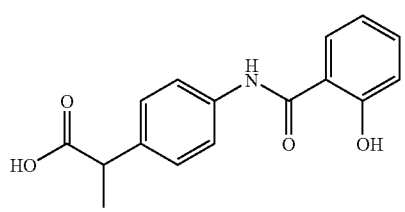

Compound 5,

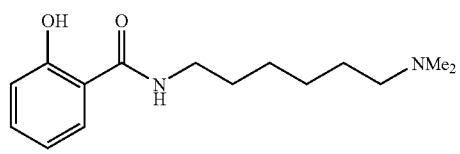

Compound 6,

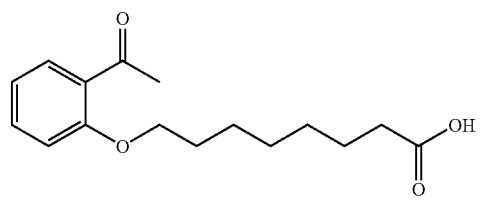

Compound 7,

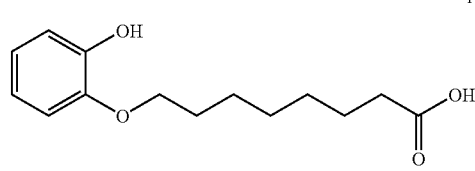

-continued

Compound 8,

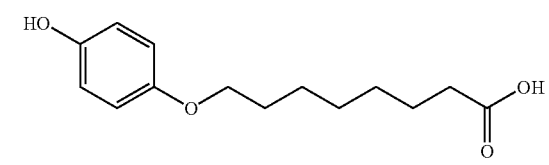

and salts thereof.

32. The composition of claim 31 wherein (B) is

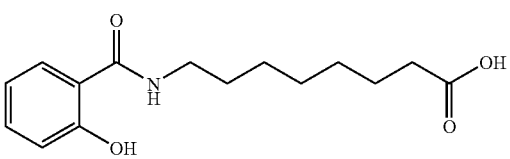

Compound 1 or a salt thereof.

33. The composition of claim 32 wherein (B) is the sodium salt of compound 1.

34. The composition of claim 31 wherein (B) is

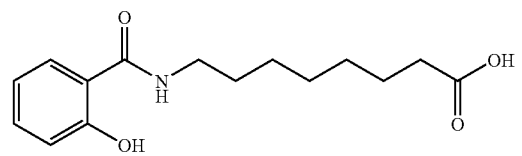

Compound 2 or a salt thereof.

35. The composition of claim 31 wherein (B) is

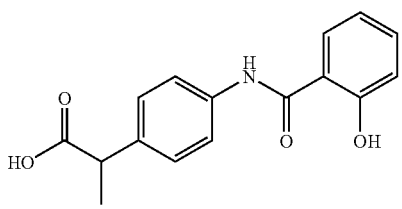

Compound 3 or a salt thereof.

36. The composition of claim 31 wherein (B) is

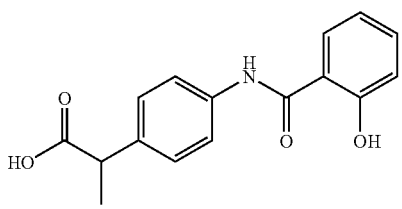

Compound 4 or a salt thereof.

37. The composition of claim 31 wherein (B) is
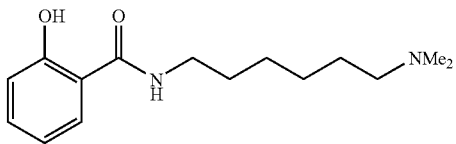
Compound 5 or a salt thereof.
38. The composition of claim 31 wherein (B) is
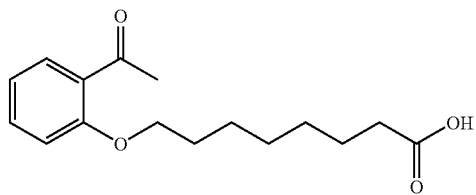
Compound 6 or a salt thereof.
39. The composition of claim 31 wherein (B) is
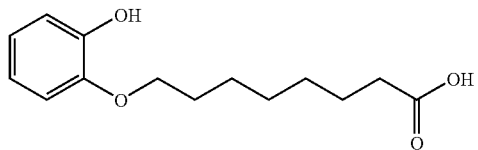
Compound 7 or a salt thereof.
40. The composition of claim 31 wherein (B) is
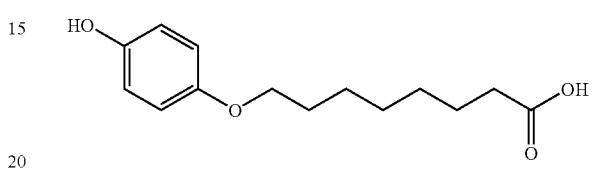
Compound 8 or a salt thereof.
* * * * *